US009085777B2

(12) United States Patent
Conner

(10) Patent No.: US 9,085,777 B2
(45) Date of Patent: Jul. 21, 2015

(54) MUTANT HSV, MATERIALS AND METHODS FOR GENERATION OF MUTANT HSV

(75) Inventor: Joe Conner, Glasgow (GB)

(73) Assignee: Virttu Biologics Limited, Glasgow (GB)

(*) Notice: Subject to any disclaimer, the term of this patent is extended or adjusted under 35 U.S.C. 154(b) by 440 days.

(21) Appl. No.: 12/299,965

(22) PCT Filed: May 4, 2007

(86) PCT No.: PCT/GB2007/001631
§ 371 (c)(1),
(2), (4) Date: Nov. 7, 2008

(87) PCT Pub. No.: WO2007/132169
PCT Pub. Date: Nov. 22, 2007

(65) Prior Publication Data
US 2009/0176203 A1 Jul. 9, 2009

(30) Foreign Application Priority Data

May 11, 2006 (GB) .................. 0609383.5
Oct. 23, 2006 (GB) .................. 0621051.2

(51) Int. Cl.
C12N 15/86 (2006.01)
C12Q 1/70 (2006.01)
C12N 7/01 (2006.01)
C12N 15/869 (2006.01)

(52) U.S. Cl.
CPC .............. C12N 15/86 (2013.01); C12N 15/869 (2013.01); C12N 15/8695 (2013.01); C12N 2710/16034 (2013.01); C12N 2710/16041 (2013.01); C12N 2710/16061 (2013.01); C12N 2710/16611 (2013.01); C12N 2710/16634 (2013.01); C12N 2710/16643 (2013.01)

(58) Field of Classification Search
CPC ............ C12N 7/00; C12N 15/86; C12N 2710/16622; C12N 2710/16632; C12N 2710/16633; C12N 2710/16641; C12N 2710/16643; C12N 2710/16671; C12N 2800/30; C12N 15/10; C12N 15/907; C12N 2800/70; C12N 15/63; C12N 2710/10343; C12N 2710/16722; C12N 2710/16711
See application file for complete search history.

(56) References Cited

U.S. PATENT DOCUMENTS

| 6,120,764 | A  | * | 9/2000  | Graham et al. ............ 424/93.6 |
| 6,248,320 | B1 | * | 6/2001  | Coffin et al. ............. 424/93.2 |
| 7,304,130 | B2 | * | 12/2007 | Hartley et al. ............ 530/350 |
| 2003/0022179 | A1 | * | 1/2003 | Chesnut et al. ............ 435/6 |
| 2003/0100110 | A1 | * | 5/2003 | Hartley et al. ............ 435/455 |
| 2004/0005710 | A1 | * | 1/2004 | Son et al. ............... 435/456 |
| 2004/0010809 | A1 | * | 1/2004 | Wolf et al. .............. 800/3 |
| 2005/0282184 | A1 | * | 12/2005 | Chesnut et al. ............ 435/6 |

OTHER PUBLICATIONS

Nakano et al (Nucleic Acids Research 33 (8): e76, pp. 1-8, 2005).*
GibcoBRL GATEWAY™ Cloning Technology Manual; Life Technologies, Feb. 2, 2002.*
Landy A. Mechanistic and structural complexity in the site-specific recombination pathways of Int and FLP. Curr Opin Genet Dev. Oct. 1993;3(5):699-707.*
Kasai, K; Saeki, Y. 156. Rapid Methods of Engineering HSV Amplicon Vectors. Mol Ther. May 2006. vol. 13: S1-S61: 1525-0016. http://dx.doi.org/10.1016/j.ymthe.2006.08.179.*
Terada et al (Gene Therapy 13:705-714, published Apr. 15, 2006; in IDS).*
Gage et al (Journal of Virology 66: 5509-5515, 1992; in IDS).*
Nakano M, Odaka K, Takahashi Y, Ishimura M, Saito I, Kanegae Y. Production of viral vectors using recombinase-mediated cassette exchange. Nucleic Acids Res. May 5, 2005;33 (8) :e76.*
Gage et al., "A Cell-Free Recombination System for Site-Specific Integration of Multigenic Shuttle Plasmids into the Herpes Simplex Virus Type 1 Genome" J. Virology (1992) 66(9):5509-5515.
Krisky et al. "Rapid Method for Construction of Recombinant HSV Gene Transfer Vectors" Gene Therapy (1997) 4:1120-1125.
Landy "Dynamic, Structural, and Regulatory Aspects of a Site-Specific Recombination" Annu. Rev. Biochem. (1989) 58:913-49.
Schmeisser and Weir "Incorporation of a Lambda Phage Recombination System and EGFP Detection to Simply Mutagenesis of Herpes Simplex Virus Bacterial Artificial Chromosomes" BMC Biotechnology (2007) 7:22.
Shen and Nemunaitis, "Herpes Simplex Virus 1 (HSV-1) for Cancer Treatment" Cancer Gene Therapy (2006) 13:975-992.

(Continued)

Primary Examiner — Benjamin P Blumel
Assistant Examiner — Rachel Gill
(74) Attorney, Agent, or Firm — Swanson & Bratschun, L.L.C.

(57) ABSTRACT

The present invention includes a method of generating a mutant Herpes Simplex Virus (HSV). In one embodiment, the generated HSV genome includes nucleic acid encoding a nucleic acid sequence of interest. In one step, a nucleic acid vector is provided which includes a nucleic acid encoding first and second site specific recombination sequences and a nucleic acid encoding a nucleic acid sequence of interest between said site specific recombination sequences an HSV is provided, the genome of which comprises third and fourth site specific recombination sequences In another step, the nucleic acid vector and HSV are contacted together with one or more recombinase enzymes capable of catalyzing site specific recombination between the site specific recombination sequences of said nucleic acid vector and said HSV. Another step includes identifying HSV containing the nucleic acid sequence of interest. In some embodiments, the methods are conducted in a cell-free system.

5 Claims, 7 Drawing Sheets

(56) References Cited

OTHER PUBLICATIONS

Terada et al., "Development of a Rapid Method to Generate Multiple Oncolytic HSV Vectors and Their In-Vivo Evaluation Using Syngeneic Tumor Models" Gene Therapy (2006) 13:705-714.

Aoki et al., "Efficient Generation of Recombinant Adenoviral Vectors by Cre-lox Recombination in Vitro", 1999, Molecular Medicine 5 pp. 224-231.

Coates et al., "Site-directed genome modification: derivatives of DNA-modifying enzymes as targeting tools", Aug. 8, 2005, Trends in Biotechnology, vol. 23, No. 8, pp. 407-419.

Hartley et al., "DNA Cloning Using in Vitro Site-Specific Recombination", 2000, Genome Research 10, pp. 1788-1795.

* cited by examiner

Rapid recombinant virus production by site-specific recombination with HSV1716 gateway HSV1716 gateway DNA with CMV-DSred in RL1 flanked by destination sites + Gene of Interest/PGK-gfp in entry vector HSV1716 DNA with Gene of Interest/PGK-gfp inserted in RL1

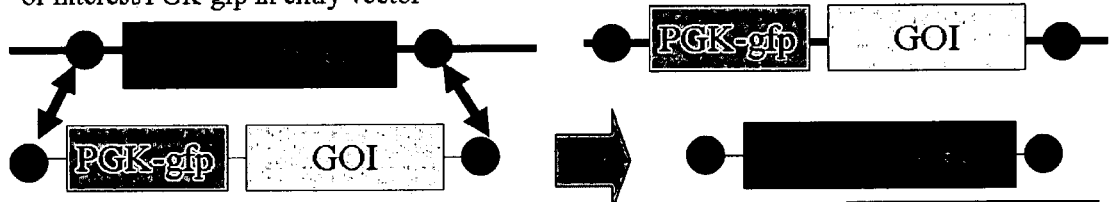

LR clonase catalyses site-specific recombination
Cells then transfected with viral DNA
75% of plaques express gfp rather than Dsred
Two rounds of plaque purification isolates HSV1716 with Gene of Interest/PGK-gfp inserted in RL1

Figure 1

MUTANT HSV, MATERIALS AND METHODS FOR GENERATION OF MUTANT HSV

RELATED APPLICATIONS

This application is a 35 USC §371 of PCT Application Serial No. PCT/GB2007/001631, filed May 4, 2007, currently pending, entitled "Mutant HSV, Materials and Methods for Generation of Mutant HSV," which claims priority to Great Britain Patent Application No. 0609383.5, filed May 11, 2006, and Great Britain Patent Application No. 0621051.2, filed Oct. 23, 2006, which are each incorporated herein in their entirety by reference.

FIELD OF THE INVENTION

The present invention relates to mutant Herpes Simplex Virus (HSV), to nucleic acid vectors, including, but not limited to HSV vectors, to methods of generating mutant HSV and to the mutant HSV generated.

BACKGROUND TO THE INVENTION

Generation of herpes simplex virus (HSV) mutants often requires generation of a unique plasmid by cloning an entire expression cassette consisting of a promoter, gene of interest and polyadenylation sequences into a plasmid separately constructed to contain the relevant flanking sequences and then co-transfecting BHK cells with the resultant plasmid and HSV-1 DNA. Homologous recombination drives the formation of recombinant HSV-1 expressing the gene of interest, which is identified by Southern blotting. The recombinant virus is plaque purified between 6-10 times by Southern blotting, dependent on the efficiency of the homologous recombination. This process can take between 3-6 months.

This approach was taken by Liu et al[1] in generating two distinct plasmids, the first consisting of HSV-1 strain 17+ Sau3A fragment derived sequences flanking an expression cassette consisting of a CytoMegalovirus (CMV) promoter, Green Fluorescent Protein (GFP) gene and bGH polyadenylation (polyA) signal and the second wherein the GFP gene is replaced with either a human or mouse Granulocyte Macrophage Colony Stimulating Factor (GM-CSF) gene.

Shuttle vectors have been used to generate recombinant adenoviral vectors, e.g. the pAdEasy™ system of vectors (Stratagene), for use in overexpressing recombinant proteins in mammalian cells. However, these vectors require the cloning of the gene of interest into a first shuttle vector which is then co-transformed into a specially constructed cell line to generate a recombinant adenoviral plasmid which is transfected into a separate specially constructed mammalian cell line in which the recombinant adenoviral plasmid is directly packaged into virus particles.

Terada et al[2] sought to introduce therapeutic transgenes into an oncolytic HSV vector backbone by creating an HSV-BAC (bacterial artificial chromosome) carrying the entire MGH1 genome and a replication-conditional shuttle plasmid.

Creation of viral vectors, particularly HSV, which may encode a gene of interest capable of being expressed from the vector, is presently a slow and often complicated and inefficient process.

The HSV genome comprises two covalently linked segments, designated long (L) and short (S). Each segment contains a unique sequence flanked by a pair of inverted terminal repeat sequences. The long repeat (RL or $R_L$) and the short repeat (RS or $R_S$) are distinct.

The HSV ICP34.5 (also γ34.5 or RL1) gene, which has been extensively studied, has been sequenced in HSV-1 strains F and syn17+ and in HSV-2 strain HG52. One copy of the ICP34.5 gene is located within each of the RL repeat regions. Mutants inactivating both copies of the ICP34.5 gene (i.e. null mutants), e.g. HSV-1 strain 17 mutant 1716 (HSV1716) or the mutants R3616 or R4009 in strain F, are known to lack neurovirulence, i.e. be avirulent, and have utility as both gene delivery vectors or in the treatment of tumours by oncolysis. HSV1716 has a 759 bp deletion in each copy of the ICP34.5 gene located within the BamHI s restriction fragment of each RL repeat.

ICP34.5 null mutants such as HSV1716 are, in effect, first-generation oncolytic viruses. Most tumours exhibit individual characteristics and the ability of a broad spectrum first generation oncolytic virus to replicate in or provide an effective treatment for all tumour types is not guaranteed.

The prior art provides technically challenging, procedurally slow and inefficient materials and methods for generating recombinant HSV. In particular the prior art does not provide methods of, and materials for, generating recombinant HSV which are easy to detect, may be designed to be specific null mutants and which may express a selected gene of interest.

First generation oncolytic viruses such as HSV-1 strain 17 mutant 1716 show significant therapeutic potential in tumour and gene therapy. Overcoming the existing technical difficulties by enabling rapid generation and screening of second generation oncolytic viruses of this kind provides a significant improvement in the development of novel pharmaceutical compositions, vaccines and medicaments for the treatment of cancer and disease.

HSV 1716 is described in EP 0571410 and WO 92/13943 and has been deposited on 28 Jan. 1992 at the European Collection of Animal Cell Cultures, Vaccine Research and Production Laboratories, Public Health Laboratory Services, Portion Down, Salisbury, Wiltshire, SP4 0JG, United Kingdom under accession number V92012803 in accordance with the provisions of the Budapest Treaty on the International Recognition of the Deposit of Microorganisms for the Purposes of Patent Procedure (herein referred to as the 'Budapest Treaty').

The HSV-1 strain 17+ mutant 1716 lacks a functional ICP34.5 gene resulting in greatly reduced lethality in mice but replicates as wild-type virus in actively dividing tissue culture cells (MacLean et al 1991, Brown et al 1994). The ICP34.5 ORF is a neurovirulence gene and its protein product has been proposed to condition post-mitotic cells for viral replication, probably via an interaction with proliferating cell nuclear antigen (Brown et al 1997, Harland et al 2003). ICP34.5 deletion mutants cannot replicate in terminally differentiated cells but lytically infect dividing cells and this effective tumour targeting strategy has allowed development of HSV1716 as a potent oncolytic therapeutic agent. HSV1716 effectively kills tumour cell lines in tissue culture and, in a range of murine cancer models, the virus has induced tumour regression and increased survival times (Kesari et al 1995, MacKie et al 1996, Randazzo et al 1997). An excellent safety profile has been demonstrated in clinical trials following direct intratumoral injection of HSV1716 in patients with recurrent glioma (Rampling et al 2000, Papanastassiou et al; 2002, Harrow et al; 2004), metastatic melanoma (MacKie et al 2001) and squamous cell carcinoma of the head and neck (Mace et al unpublished). In each of these trials there was no evidence for spread of HSV1716 to surrounding normal tissue and the selectivity of the virus for replication in tumour cells alone has immense therapeutic potential for the treatment of many human malignancies. Currently, HSV1716 has been awarded orphan drug status for treatment of recurrent glioma and a Phase II/III clinical trial has recently been initiated.

The expression of exogenous genes such as enzymes for prodrug activation or transporters for the uptake of radioactive compounds will augment the oncolytic activity of HSV1716 by enhancing its ability to destroy tumour cells. Two such variants, HSV1716/NAT, which expresses the noradrenaline transporter (NAT) for the specific uptake of radiolabelled compounds such as [$^{131}$I]MIBG, and HSV1790, that expresses nitroreductase, an enzyme capable of activating the prodrug CB1954, have respectively enhanced glioma cell cytotoxicity in tissue culture (Quigg et al, 2005). HSV1716/NAT and HSV1790 were generated by homologous recombination using an RL-1 shuttle vector that contained the NAT/nitroreductase expression cassette inserted within the ICP34.5 deleted region; cotransfection of BHK cells with the shuttle plasmid and HSV-1 strain 17+ DNA resulted in homologous recombination at the RL-1 loci with the resultant virus possessing an HSV1716 backbone with a NAT/nitroreductase expression cassette within the ICP34.5 deletion. However, homologous recombination is relatively inefficient with recombinant viruses produced in low numbers and isolation requires many rounds of time-consuming plaque purification to remove residual wild-type virus. For the development of an accelerated vector programme, which will allow production of large numbers of different second generation HSV1716 variants to be screened for enhanced tumour destruction, it will be advantageous to create recombinant viruses more rapidly and efficiently.

HSV1790 (also called HSV1716/CMV-NTR/GFP) is described in WO 2005/049845 and has been deposited in the name of Crusade Laboratories Limited having an address at Department of Neurology Southern General Hospital 1345 Govan Road Govan Glasgow G51 5TF Scotland on 5 Nov. 2003 at the European Collection of Cell Cultures (ECACC), Health Protection Agency, Porton Down, Salisbury, Wiltshire, SP4 0JG, United Kingdom under accession number 03110501 in accordance with the provisions of the Budapest Treaty on the International Recognition of the Deposit of Microorganisms for the Purposes of Patent Procedure (herein referred to as the 'Budapest Treaty').

SUMMARY OF THE INVENTION

The lambda phage site-specific recombination system employs a recombinase enzyme to exchange DNA sequences flanked by site-specific DNA recognition sequences and provides an alternative to conventional restriction enzyme/DNA ligase-based cloning/subcloning.

The gene/DNA sequence of interest is inserted into an entry plasmid at a multi-cloning site flanked by attL site-specific recombination sequences. The gene/DNA sequence of interest in the entry vector is incubated in vitro with a destination plasmid and the enzyme LR clonase (Invitrogen, Carlsbad, Calif., USA) catalyses the exchange of the gene/DNA sequence from the entry vector to a desired site in the destination vector which is flanked by attR sequences.

The inventors developed this system in an attempt to improve the production of HSV mutants and discovered that the method allows very rapid and highly efficient production of viral recombinants. Taking account of the large size of the HSV genome (circa. 152 kbp) it was surprising to find that this site specific recombination technique worked so efficiently in a cell free system in vitro.

The general strategy developed by the inventors is to create an HSV destination vector containing site specific recombination sequences (preferably a pair of them) at a selected location in the HSV genome. This may be achieved by directing homologous recombination of a nucleotide sequence or cassette into the HSV genome through the use of selected HSV flanking sequences to drive the homologous recombination event. Conditions for homologous recombination may be provided by using cells in culture undergoing replication.

Once generated, the mutant HSV (sometimes called the destination vector) can be used as a model HSV for the generation of a range of other specific HSV mutants each having a different sequence introduced at the chosen location. This is achieved by contacting the HSV destination vector with an entry vector having a nucleotide sequence of interest flanked by corresponding site specific recombination sites. The recombination reaction between the site specific recombination sequences may be conducted in an in vitro cell-free system, not requiring cell culture.

By directing the entry of the nucleotide sequence of interest to the same location in the HSV genome each of the generated HSV mutants can be a mutant of the same type (e.g. gene specific null mutant) but may differ owing to the nature (and expression) of the nucleotide sequence of interest. This general strategy is illustrated in FIG. 7.

The present invention provides a method of generating HSV mutants using site specific recombination and also provides HSV capable of being used for generation of such HSV mutants and the HSV mutants generated.

According to one aspect of the present invention there is provided a Herpes simplex virus genome comprising one or more site specific recombination sequences.

The site specific recombination sequences are preferably capable of being recognised by one or more recombinase enzymes. The HSV genome preferably encodes one or more non-HSV originating site specific recombination sequences. The HSV may have been modified, e.g. as compared to the wild type HSV genome, in order to introduce the site specific recombination sites. Such modification may be carried out by any appropriate technique, e.g. insertion, addition or replacement of nucleic acid.

The HSV genome preferably further comprises a DNA sequence encoding a nucleic acid of interest that is flanked by first and second site specific recombination sequences.

The nucleic acid of interest may encode a marker, which may be operably linked to a regulatory sequence.

The nucleic acid of interest may, additionally or alternatively to encoding the marker and optional regulatory sequence, preferably encode a non-HSV originating polypeptide, which may be operably linked to a regulatory sequence.

Accordingly, the HSV genome may preferably comprise a nucleic acid cassette, said cassette comprising first and second site specific recombination sequences flanking DNA sequence encoding a marker and DNA sequence encoding a non-HSV originating polypeptide Aspects of the invention therefore include:

An HSV genome comprising a DNA sequence encoding a marker polypeptide flanked by first and second site specific recombination sequences.

An HSV genome comprising a DNA sequence encoding a non-HSV originating polypeptide flanked by first and second site specific recombination sequences.

An HSV genome comprising a nucleic acid cassette, said cassette comprising first and second site specific recombination sequences flanking DNA sequence encoding a marker and DNA sequence encoding a non-HSV originating polypeptide.

HSV according to the invention may be gene-specific mutants (preferably null mutants) in which site specific recombination results in disruption of a gene of interest (in one or each copy), preferably by insertion of nucleic acid but optionally by deletion, such that the HSV is not capable of expressing corresponding functional protein.

DNA encoding the marker and/or the non-HSV originating polypeptide is preferably operably linked to a regulatory sequence, e.g. promoter, which preferably forms part of the DNA sequence flanked by the site specific recombination sequences. The marker and non-HSV originating sequence may be operably linked to the same or separate regulatory sequences.

HSV according to the present invention may be vectors, e.g. expression and/or transcription vectors, for use in expression of a gene of interest, e.g. a non-HSV originating polypeptide that is exogenous to the HSV. Such HSV may be provided for use in expression of the gene product in vivo or in vitro and may be used in gene therapy techniques for the treatment of disease.

In a further aspect of the present invention there is provided a method of generating a mutant HSV, wherein the generated HSV genome comprises DNA encoding a nucleic acid sequence of interest, the method comprising the steps of:
i. providing a nucleic acid vector comprising nucleic acid encoding first and second site specific recombination sequences and a nucleic acid encoding a nucleic acid sequence of interest between said site specific recombination sequences;
ii. providing an HSV, the genome of which comprises third and fourth site specific recombination sequences;
iii. contacting said nucleic acid vector of (i) with said HSV of (ii) together with one or more recombinase enzymes capable of catalysing site specific recombination between the site specific recombination sequences of said nucleic acid vector and said HSV;
iv. identifying HSV containing the nucleic acid sequence of interest.

The method is preferably an in vitro method. Steps i-iii may be conducted in a cell-free system. Recombinant mutant HSV may be identified in step iv by infection of cell culture with virus and identification of HSV plaques expressing the nucleic acid sequence of interest.

The nucleic acid vector of (i) may be called the entry vector. The HSV of (ii) may be called the destination vector.

The method may be employed for the generation of HSV mutants in which the HSV genome is modified by site specific insertion of the nucleic acid sequence of interest. Such methods may be used to generate a range of mutant HSV including gene-specific null mutants and/or HSV capable of expressing therapeutic transgenes, e.g. for use in gene therapy techniques.

The nucleic acid sequence of interest may be any sequence, preferably DNA, encoding a non-HSV originating polypeptide and may comprise a marker and/or a therapeutic transgene, either or both of which may be operably linked to a regulatory element, e.g. promoter. The mutant HSV generated is, therefore, preferably capable of expressing the nucleic acid sequence of interest.

Preferably, the nucleic acid vector of (i) may be the plasmid RL1.del modified to incorporate nucleic acid encoding the first and second site specific recombination sequences and a nucleic acid encoding a nucleic acid sequence of interest between said site specific recombination sequences. This modification may be achieved by insertion of these sequences at the multi-cloning site in RL1.del.

RL1.del (FIG. 2) is the pGEM-3Zf(−) plasmid (Promega) into which has been cloned an HSV-1 fragment (123459-129403) consisting of the RL1 (ICP34.5 gene) gene and its flanking sequences. The 477 bp PflMI-BstEII fragment of the RL1 gene (125292-125769) was removed and replaced with a multi-cloning site (MCS) to form RL1.del.

The modified RL1.del vector may be used in a method of generating HSV ICP34.5 mutants (preferably null mutants) wherein the nucleic acid sequence of interest is inserted so as to disrupt the mRNA and/or protein coding sequence of the ICP34.5 gene such that the gene product is inactive in the resultant mutant virus.

The modified RL1.del plasmid forms a further aspect of the present invention.

By selecting the flanking sequences in the modified RL1.del vector to correspond with HSV genomic sequences from a selected HSV gene it is possible to create other vectors that may be used in the generation of gene-specific HSV mutants (optionally null mutants). Such vectors also form further aspects of the present invention.

In another preferred arrangement the nucleic acid vector of (i) may be a plasmid vector in which the first and second site specific recombination sequences flank the sequence of interest.

The present invention includes methods for the generation of mutant HSV (destination vector) in which site specific recombination sequences are present at selected locations in the HSV genome.

In one particularly preferred arrangement this HSV is generated by:
a) providing a nucleic acid encoding a nucleotide sequence having 70-100% sequence identity or complementarity with a selected region of the HSV genome;
b) inserting first and second site specific recombination sequences in the nucleotide sequence of a) to generate a modified nucleic acid vector;
c) contacting said modified nucleic acid vector from b) with a selected HSV genome, under conditions in which homologous recombination between said nucleic acid vector and HSV genome may occur;
d) identifying HSV containing said first and second site specific recombination sequences in the HSV genome.

Steps a)-c) are preferably carried out in vivo in cell culture in order to provide suitable conditions for homologous recombination.

The nucleotide sequence in a) is preferably capable of hybridising with the selected region of the HSV genome under intermediate, high or very high stringency conditions. Preferably, the nucleotide sequence in a) is part or all of a gene sequence from the selected HSV genome, e.g. the RL1 gene or coding sequence.

The degree of sequence identity/complementarity in a) may preferably be one of at least 80%, 85%, 90%, 95%, 96%, 97%, 98%, 99% or may be 100%.

The HSV generated by this method form part of the present invention.

HSV according to the present invention, including those generated by, or used in, the methods of the present invention are preferably not part of an artificial chromosome, such as a BAC (bacterial artificial chromosome) or YAC (yeast artificial chromosome). In contrast, the HSV preferably have a genome that functions (e.g. replicates) in an independent manner that corresponds with other wild type HSV.

The site specific recombination sequences are preferably DNA. The site specific recombination sequences may be short and are preferably less than 500 nucleotides in length, more preferably less than 300 nucleotides, still more preferably less than 150 nucleotides. Preferred site specific recombination sequences are those not normally occurring in the HSV genome, e.g. in the respective wild type HSV genome.

By way of example, preferred sequences include the 125 nucleotide attR sequences, attR1 and attR2, and the 100 nucleotide attL sequences, attL1 and attL2:

```
attR1
                                           (SEQ ID No.1)
ACAAGTTTGTACAAAAAAGCTGAACGAGAAACGTAAAATGATATAAATAT

CAATATATTAAATTAGATTTTGCATAAAAAACAGACTACATAATACTGTA

AAACACAACATATCCAGTCATATTG attR2
                                           (SEQ ID No.2)
CATAGTGACTGGATATGTTGTGTTTTACAGCATTATGTAGTCTGTTTTTT

ATGCAAAATCTAATTTAATATATTGATATTTATATCATTTTACGTTTCTC

GTTCAGCTTTCTTGTACAAAGTGGT attL1
                                           (SEQ ID No.3)
CAAATAATGATTTTATTTTGACTGATAGTGACCTGTTCGTTGCAACAAAT

TGATAAGCAATGCTTTTTTATAATGCCAACTTTGTACAAAAAAGCAGGCT attL2
                                           (SEQ ID No.4)
ACCCAGCTTTCTTGTACAAAGTTGGCATTATAAGAAAGCATTGCTTATCA

ATTTGTTGCAACGAACAGGTCACTATCAGTCAAAATAAAATCATTATTTG
``` attR1 and attR2 may form one pair of flanking sequences, e.g. in an HSV destination vector, and attL1 and attL2 may form a second pair of flanking sequences, e.g. in a nucleic acid entry vector.

Most preferably, the HSV genome will contain two site specific recombination sequences flanking a portion of a selected HSV gene. The genome may contain more than one copy of the selected HSV gene which is being targeted, e.g. for inactivation by insertion of DNA. Accordingly, two site specific recombination sequences may be provided at the locus of each copy of the respective gene. Thus, in some preferred arrangements the HSV genome will contain 4 copies of the site specific recombination sequences.

The site specific recombination sequences may be located at any selected part of the HSV genome. The site specific recombination sequences may be located so as to flank all or part of a genome sequence encoding the mRNA, or protein, of a selected HSV gene. For example, one of the site specific recombination sequences may be located within such mRNA or protein coding sequence and the other site specific recombination sequence may be located upstream or downstream, and outside, of the respective coding sequence or HSV gene. One or both site specific recombination sequences may be located within the mRNA encoding, or protein coding, sequence of the selected HSV gene. Alternatively, both sites may be located outside mRNA or protein coding sequences but within regulatory sequences, such as promoters, of the HSV genome.

In the HSV genome the site specific recombination sequences may be located so as to define a predetermined spacing between those sequences of any length.

A marker may be a defined nucleotide sequence and may encode a selected polypeptide, preferably a non-HSV originating polypeptide.

In one arrangement the marker may comprise the Green Fluorescent Protein (GFP) protein coding sequence or the enhanced Green Fluorescent Protein (EGFP) protein coding sequence. In another arrangement the marker may comprise the DSRed-Monomer Fluorescent Protein (Clontech).

In another arrangement the marker may comprise a defined nucleotide sequence detectable by hybridisation under high or very high stringency conditions with a corresponding labelled nucleic acid probe. Alternatively, the marker may be an enzyme coding sequence, such as the beta-galactosidase gene.

The marker may be operably linked to a regulatory sequence, e.g. a promoter enabling the marker sequence to be transcribed and expressed. The marker, and optional regulatory sequence, may form part of a nucleic acid cassette comprising nucleic acid, preferably DNA, in which the site specific recombination sequences flank the marker and regulatory sequence.

HSV and vectors according to the invention may comprise nucleic acid encoding a selected polypeptide or protein. The polypeptide is preferably one that does not originate in the HSV. Preferred polypeptides/proteins may include insulin (as insulin, preproinsulin or proinsulin) Factor VIII, Nitroreductase, and Noradrenaline Transporters. The polypeptide/protein may be human or mammalian.

In this specification, references to nucleic acid include DNA and/or RNA, more preferably DNA.

HSV according to the invention may be mutants of any strain of HSV-1 or HSV-2, preferably HSV-1. Preferred strains include strain 17, and strain F, most preferably HSV-1 strain 17.

Site Specific Recombination

Site specific recombination uses short specific nucleotide sequences that are recognised by recombinase enzymes and provide unique and specific sites for recombinase catalysed recombination of nucleic acid.

Site specific recombination involves a crossover event that requires homology of only a very short region and uses one or more enzymes specific for that recombination (the recombinases). The recombination can occur between two specific sequences that need not be homologous; mediated by a specific recombination system.

Recombinase enzymes may include enzymes that catalyse both excision and integration of nucleic acid. The recombinase enzymes may be provided with other factors that facilitate the site specific recombination. For example, bacteriophage lambda recombination proteins Integrase (Int) and Excisionase (Xis) may be required for site specific recombination between attL and attR sequences and the *E. coli*-encoded protein Integration Host Factor (IHF) may be required in order to facilitate the reaction.

The tyrosine recombinase family catalyses recombination reactions using a common mechanism involving formation of a covalent bond with an active site tyrosine residue, e.g. Int (bacteriophage lambda), XerD (*E. coli*), Cre/loxP (bacteriophage P1), FLP/FRT (yeast).

Site specific recombination sequences and the recombinase enzymes and factors required to achieve recombination are well known to those of skill in the art. For example, reference may be made to the following, all of which are incorporated herein by reference:

Chen, J. W., J. Lee, and M. Jayaram. (1992). "DNA cleavage in trans by the active site tyrosine during Flp recombination: switching protein partners before exchanging strands." *Cell* 69(4):647-58.

Chen, J. W., S. H. Yang, and M. Jayaram. (1993). "Tests for the fractional active-site model in Flp site-specific recombination. Assembly of a functional recombination complex in half-site and full-site strand transfer." *J. Biol. Chem.* 268(19):14417-25.

Kimball, A. S., J. Lee, M. Jayaram, and T. D. Tullius. (1993). "Sequence-specific cleavage of DNA via nucleophilic attack of hydrogen peroxide, assisted by Flp recombinase." *Biochemistry* 32(18):4698-701.

Lee, J., and M. Jayaram. (1997). "A tetramer of the Flp recombinase silences the trimers within it during resolution of a Holliday junction substrate." *Genes Dev.* 11(18): 2438-47.

Lee, J., T. Tonozuka, and M. Jayaram. (1997). "Mechanism of active site exclusion in a site-specific recombinase: role of the DNA substrate in conferring half-of-the-sites activity." *Genes Dev.* 11(22):3061-71.

Xu, C. J., I. Grainge, J. Lee, R. M. Harshey, and M. Jayaram. (1998). "Unveiling two distinct ribonuclease activities and a topoisomerase activity in a site-specific DNA recombinase."*Mol. Cell.* 1(5): 729-39.

Sau A K, DeVue Tribble G, Grainge I, Frohlich R F, Knudsen B R, Jayaram M. (2001). "Biochemical and kinetic analysis of the RNase active sites of the integrase/tyrosine family site-specific DNA recombinases." *J. Biol. Chem.* 276(49): 46612-23.

Grainge I., Buck D., Jayaram M. (2000). "Geometry of site alignment during int family recombination: antiparallel synapsis by the Flp recombinase." *J. Mol. Biol.* 298(5): 749-64.

Grainge I, Pathania S, Vologodskii A, Harshey R M, Jayaram M. (2002). "Symmetric DNA sites are functionally asymmetric within Flp and Cre site-specific DNA recombination synapses." *J. Mol. Biol.* 320(3):515-27.

Operably Linked

In this specification the term "operably linked" may include the situation where a selected nucleotide sequence and regulatory nucleotide sequence are covalently linked in such a way as to place the expression of a nucleotide sequence under the influence or control of the regulatory sequence. Thus a regulatory sequence is operably linked to a selected nucleotide sequence if the regulatory sequence is capable of effecting and/or controlling transcription of a nucleotide sequence which forms part or all of the selected nucleotide sequence. Where appropriate, the resulting transcript may then be translated into a desired protein or polypeptide.

Neurovirulence

In this specification, non-neurovirulence is defined by the ability to introduce a high titre of virus (approx $10^6$ plaque forming units (pfu)) to an animal or patient without causing a lethal encephalitis such that the $LD_{50}$ in animals, e.g. mice, or human patients is in the approximate range of $\geq 10^6$ pfu.

Therapeutic Applications

HSV according to the present invention may be provided for use in a medical method, e.g. for the treatment of disease in a patient. The use of HSV according to the present invention in the manufacture of a medicament for the treatment of disease is also provided. ICP34.5 null HSV according to the invention may be provided for use in the treatment of a cancerous condition.

A cancerous condition may be any unwanted cell proliferation (or any disease manifesting itself by unwanted cell proliferation), neoplasm or tumour or increased risk of or predisposition to the unwanted cell proliferation, neoplasm or tumour. The cancerous condition may be a cancer and may be a benign or malignant cancer and may be primary or secondary (metastatic). A neoplasm or tumour may be any abnormal growth or proliferation of cells and may be located in any tissue. Examples of tissues include the colon, pancreas, lung, breast, uterus, stomach, kidney, testis, central nervous system (including the brain), peripheral nervous system, skin, blood or lymph.

The HSV for use in the present invention may be formulated as pharmaceutical compositions for clinical use and may comprise a pharmaceutically acceptable carrier, diluent or adjuvant. The composition may be formulated for topical, parenteral, systemic, intravenous, intra-arterial, intramuscular, intrathecal, intraocular, intratumoural, subcutaneous, oral or transdermal routes of administration which may include injection. Injectable formulations may comprise the selected compound in a sterile or isotonic medium.

Administration is preferably in a "therapeutically effective amount", this being sufficient to show benefit to the individual. The actual amount administered, and rate and time-course of administration, will depend on the nature and severity of the disease, e.g. tumour, being treated. Prescription of treatment, e.g. decisions on dosage etc, is within the responsibility of general practitioners and other medical doctors, and typically takes account of the disorder to be treated, the condition of the individual patient, the site of delivery, the method of administration and other factors known to practitioners. Examples of the techniques and protocols mentioned above can be found in Remington's Pharmaceutical Sciences, 20th Edition, 2000, pub. Lippincott, Williams & Wilkins.

Alternatively, targeting therapies may be used to deliver the active agent more specifically to certain types of cell, by the use of targeting systems such as antibody or cell specific ligands. Targeting may be desirable for a variety of reasons; for example if the agent is unacceptably toxic, or if it would otherwise require too high a dosage, or if it would not otherwise be able to enter the target cells.

HSV capable of targeting cells and tissues are described in (PCT/GB2003/000603; WO 03/068809), hereby incorporated in its entirety by reference.

A composition may be administered alone or in combination with other treatments, either simultaneously or sequentially dependent upon the condition to be treated.

The patient to be treated may be any animal or human. The patient may be a non-human mammal, but is more preferably a human patient. The patient may be male or female.

Hybridisation Stringency

In accordance with the present invention, nucleic acid sequences may be identified or defined by using hybridization and washing conditions of appropriate stringency.

Complementary nucleic acid sequences will hybridise to one another through Watson-Crick binding interactions. Sequences which are not 100% complementary may also hybridise but the strength of the hybridisation usually decreases with the decrease in complementarity. The strength of hybridisation can therefore be used to distinguish the degree of complementarity of sequences capable of binding to each other.

The "stringency" of a hybridization reaction can be readily determined by a person skilled in the art.

The stringency of a given reaction may depend upon factors such as probe length, washing temperature, and salt concentration. Higher temperatures are generally required for proper annealing of long probes, while shorter probes may be annealed at lower temperatures. The higher the degree of desired complementarity between the probe and hybridisable sequence, the higher the relative temperature which can be used. As a result, it follows that higher relative temperatures would tend to make the reaction conditions more stringent, while lower temperatures less so.

For example, hybridizations may be performed, according to the method of Sambrook et al., ("Molecular Cloning, A Laboratory Manual, Cold Spring Harbor Laboratory Press, 1989) using a hybridization solution comprising: 5×SSC, 5×Denhardt's reagent, 0.5-1.0% SDS, 100 µg/ml denatured, fragmented salmon sperm DNA, 0.05% sodium pyrophosphate and up to 50% formamide. Hybridization is carried out at 37-42° C. for at least six hours. Following hybridization, filters are washed as follows: (1) 5 minutes at room temperature in 2×SSC and 1% SDS; (2) 15 minutes at room temperature in 2×SSC and 0.1% SDS; (3) 30 minutes-1 hour at 37° C. in 1×SSC and 1% SDS; (4) 2 hours at 42-65° C. in 1×SSC and 1% SDS, changing the solution every 30 minutes.

One common formula for calculating the stringency conditions required to achieve hybridization between nucleic acid molecules is to calculate the melting temperature $T_m$ (Sambrook et al., 1989):

$$T_m=81.5°\ C.+16.6\ \text{Log}\ [Na+]+0.41(\%\ G+C)-0.63(\%\ \text{formamide})-600/n$$

where n is the number of bases in the oligonucleotide.

As an illustration of the above formula, using [Na+]= [0.368] and 50% formamide, with GC content of 42% and an average probe size of 200 bases, the $T_m$ is 57° C. The $T_m$ of a DNA duplex decreases by 1-1.5° C. with every 1% decrease in sequence complementarity.

Accordingly, nucleotide sequences can be categorised by an ability to hybridise to a target sequence under different hybridisation and washing stringency conditions which can be selected by using the above equation. The $T_m$ may be used to provide an indicator of the strength of the hybridisation.

The concept of distinguishing sequences based on the stringency of the conditions is well understood by the person skilled in the art and may be readily applied.

Sequences exhibiting 95-100% sequence complementarity are considered to hybridise under very high stringency conditions, sequences exhibiting 85-95% complementarity are considered to hybridise under high stringency conditions, sequences exhibiting 70-85% complementarity are considered to hybridise under intermediate stringency conditions, sequences exhibiting 60-70% complementarity are considered to hybridise under low stringency conditions and sequences exhibiting 50-60% complementarity are considered to hybridise under very low stringency conditions.

DESCRIPTION OF PREFERRED EMBODIMENTS

In a preferred embodiment the HSV site specific recombination sequences are located in the HSV genome so as to disrupt or flank DNA sequence that includes part, or all, of the mRNA or protein coding sequence of the ICP34.5 gene. Two copies of the ICP34.5 gene are normally present in HSV, therefore the HSV genome may contain 4 copies of the site specific recombination sequences—one pair of site specific recombination sequences at each ICP34.5 (RL1) locus.

One or more of the site specific recombination sequences may be located within the RL1 gene so as to disrupt the ICP34.5 coding sequence and prevent expression of a functional ICP34.5 protein.

HSV ICP34.5 null mutants, i.e. that are incapable of expressing functional ICP34.5 protein, are known to be non-neurovirulent. Accordingly, they provide the basis for developing safe and effective viral vectors which find application in gene therapy techniques.

Furthermore some HSV ICP34.5 null mutants are capable of oncolysis and may be used in the treatment of tumours of all types.

Accordingly, non-neurovirulent HSV are provided according to the invention which contain a nucleic acid cassette that disrupts the mRNA and/or protein coding sequence of each copy of the ICP34.5 gene, thereby rendering the HSV incapable of producing functional ICP34.5 protein and non-neurovirulent, wherein the nucleic acid cassette is formed by a DNA sequence flanked by site specific recombination sequences. The DNA sequence may comprise a marker sequence, optionally together with an operably linked regulatory sequence, e.g. promoter. The DNA sequence may additionally, or alternatively, comprise DNA encoding a non-HSV originating polypeptide, which may also be operably linked to a regulatory sequence, e.g. promoter.

In other preferred embodiments, the HSV site specific recombination sequences are located in the HSV genome so as to disrupt and/or flank DNA sequence that includes part, or all, of the mRNA encoding, or protein coding, sequence of any selected HSV gene (in one or both copies of the gene as appropriate). Examples of such HSV genes include thymidine kinase, ribonucleotide reductase, ICP0 (also called IE1, IE110, RL2, Vmw110), ICP4 (also called IE175) and ICP27 (also called UL54). Replication and/or infection defective HSV may be provided by disrupting the ICP4 and/or ICP27 genes.

FIG. 7A-E illustrates the process of creation of the non-neurovirulent HSV destination vector (E) containing the site specific recombination sites in the HSV genome so as to disrupt the RL1 gene sequence and render the HSV incapable of producing functional ICP34.5 protein. In preferred embodiments this process of homologous recombination is conducted in cell culture.

FIG. 7F-G illustrate the use of the HSV destination vector to incorporate a nucleotide sequence of interest (e.g. gene of interest: GOI) from an entry vector containing corresponding site specific recombination sequences flanking the sequence of interest. In preferred embodiments this process of site specific recombination is conducted in a cell-free system using recombinase enzymes suitable for recombination between the selected site specific recombination sequences.

The invention includes the combination of the aspects and preferred features described except where such a combination is clearly impermissible or expressly avoided.

Aspects and embodiments of the present invention will now be illustrated, by way of example, with reference to the accompanying figures. Further aspects and embodiments will be apparent to those skilled in the art. All documents mentioned in this text are incorporated herein by reference.

BRIEF DESCRIPTION OF THE FIGURES

Embodiments and experiments illustrating the principles of the invention will now be discussed with reference to the accompanying figures in which:

FIG. 1

Figure 2:
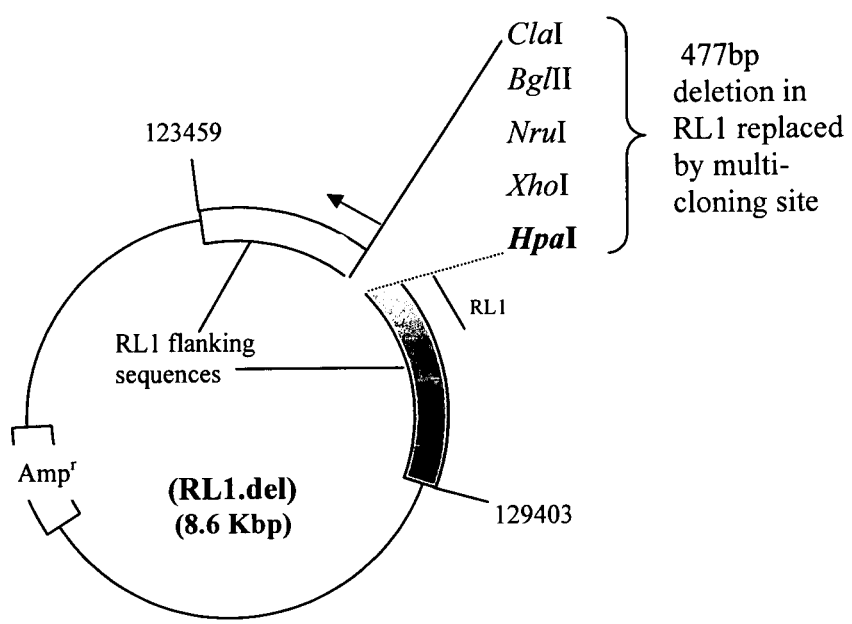

Diagram Illustrating Rapid Recombinant Virus Production by Site-Specific Recombination.

HSV1716gateway virus destination vector DNA containing CMV-DSred (CytoMeaglovirus promoter—DS red) nucleic acid in the ICP34.5 (RL1) locus and flanked by the attR site specific recombinantion sites is mixed with entry vector nucleic acid encoding a gene of interest (GOI) and PGK-gfp (Phosphogylcerokinase promoter—Green Fluorescent Protein) flanked by attL site specific recombination sequences together with LR Clonase™ II Enzyme Mix to catalyse site specific recombination.

FIG. 2

Diagram Showing Structure of RL1.del.

RL1.del is the pGEM-3Zf(−) plasmid (Promega) into which has been cloned an HSV-1 fragment (123459-129403) consisting of the RL1 (ICP34.5 gene) gene and its flanking sequences. The 477 bp PflMI-BstEII fragment of the RL1 gene (125292-125769) has been removed and replaced with a multi-cloning site (MCS) to form RL1.del.

FIG. 3

Southern Blot of Viral DNAs Probed with an ICP34.5 DNA Probe.

DNA from HSV17+ (lane 1), HSV1716 (lane 2), mock (lane 3) or HSV1716GateRed (lanes 4 and 5) infected BHK cells was extracted 24 hours post infection using the Wizard SV Genomic DNA kit (Promega, Southampton, UK) and digested overnight with BamHI. After separation on a 1% agarose gel, DNA was transferred to a nylon membrane and probed using the AluI/RsaI ICP34.5 DNA fragment from plasmid pGEM34.5 (McKie et al 1994). Molecular sizes are indicated on the left hand side of the gel and the k, s and q fragments hybridizing with the ICP34.5 probe from BamHI digested HSV-1 17+DNA, their equivalents, k* and s*, from HSV1716 DNA and the bands from HSV1716GateRed resulting from the insertion of a novel Bam HI site are indicated by arrows.

FIG. 4

Fluorescent Microscope Images Showing Red or Green Viral Plaques after Various Recombination Reactions.

Panels a-c show results from 1, 3 or 4 μg HSV1716GateRed DNA incubated with 7, 5, 4 μg respectively of the Gateway entry plasmid pENTR1A modified to express gfp. Panels d and e show results from incubation of 5 μg HSV1716GateRed DNA or 8 μg modified pENTR1A alone with the site specific recombination enzyme mix and panel f shows results from homologous recombination between 100 μg HSV1716GateRed DNA and 50 μg pRL1-del containing a gfp expression cassette. Panels g and h show results from site specific recombination reactions between 3 μg HSV1716GateRed DNA and 5 μg modified pENTR1A with 500 bp or 2000 bp inserts respectively.

FIG. 5

1% agarose gel showing products obtained by RL1 PCR using HSV-1 17+ (lane 1), HSV1716 (lane 2) and HSV1716 variants isolated after site specific recombination using pENTR1A-gfp alone (lane 3) or pENTR1A-gfp with additional 250 bp (lane 4), 500 bp (lane 5), 1500 bp (lane 6), 2000 bp (lane 7) DNA inserts. Lane M indicates the 2 log DNA ladder with the sizes of the principal bands indicated on the left hand side and lane 8 is a negative control comprising mock infected BHK cell DNA as template.

FIG. 6

Fluorescent microscope images which demonstrate the ease with which novel recombinant HSV1716 variants can be identified after the site specific recombination reaction in vitro. Panel A shows a red plaque produced by virus resulting from virus derived from the input HSV1716GateRed DNA, panel B shows a mixed yellow plaque produced from viruses derived from the input HSV1716GateRed DNA and the DNA resulting from the site specific recombination reaction and panel C shows a green plaque produced by virus derived from the DNA resulting from the site specific recombination reaction.

FIG. 7

Schematic Diagram Illustrating Creation of HSV Destination Vector and Use in Generating Other Mutant HSV.

(A) Plasmid RL1-del comprising the RL1 gene sequence with inserted multi-cloning site (MCS);
(B) Plasmid sp73 containing the CMV-DSRed sequence flanked by site specific recombination sequences (attR);
(C) The attR-CMV-DSRed cassette is excised from plasmid sp73 by restriction digestion and inserted at the MCS in plasmid RL1-del to form a modified RL1-del plasmid which is contacted with the selected HSV-1 genome (D) under conditions in which homologous recombination between the RL1 sequence components may occur to form the HSV mutant HSV1716GateRed (E) which is the non-neurovirulent 'destination vector' encoding the DSRed fluorescence marker protein operably linked to the CMV promoter. The destination vector is contacted with a selected entry vector plasmid (pEnt) (F) containing the nucleotide sequence of interest (GOI) flanked by site specific recombination sequences (attL) corresponding to those contained in the destination vector in the presence of recombinase enzymes to produce the desired non-neurovirulent HSV mutant (HSV-1716GOI) (G).

DETAILED DESCRIPTION OF THE INVENTION

Specific details of the best mode contemplated by the inventors for carrying out the invention are set forth below, by way of example. It will be apparent to one skilled in the art that the present invention may be practiced without limitation to these specific details.

EXAMPLE 1

Method

A destination site was produced in the plasmid sp73 by ligating attR sites (available from Invitrogen, Carlsbad, Calif., USA as a Gateway™ Vector conversion system) into the EcoRV-digested and alkaline phosphatase treated vector. Once inserted, the DNA (encoding chloramphenicol resistance and the ccdB gene) between the attR sites was removed by restriction enzyme digestion and replaced with a CMV-DSred expression cassette (Clontech). The attR sites and intervening CMV-DSred expression cassette was then excised from sp73 and ligated into the BglII site in the 'Smart plasmid' RL1-del (FIG. 2), used for the production of HSV ICP34.5 null mutants by homologous recombination, and this was used to create a Herpes Simplex Virus designated "HSV1716GateRed" which contains the CMV-DSred expression cassette flanked by attR sites in the RL1 loci. HSV1716GateRed DNA was then isolated and used for site-specific recombination in vitro.

RL1-del is shown in FIG. 2 and is previously described in PCT/GB2004/04839 (WO 2005/049844), incorporated herein in its entirety by reference.

The plasmid pENTR1A (Invitrogen, Carlsbad, Calif., USA) was used to create a modified entry vector, pENTR1A-gfp with the DNA between the attL sites in pENTR1A removed by EcoR1 digestion and replaced with the PGK-gfp (Phosphoglycerokinase promoter—Green Fluorescent Protein) expression cassette. Although EcoR1 removes the ccdB gene from pENTR1A, a number of other restriction sites between the attL flanking sequences are retained and these can be used to insert the gene/DNA sequence of interest to be cloned into HSV alongside the PGK-gfp expression cassette between the attL flanking sequences.

HSV recombinants are then generated by incubating HSV1716GateRed DNA with the gene/DNA sequence of interest in the pENTR1A-gfp plasmid and the recombinase enzyme Gateway™ LR Clonase™ II Enzyme Mix (Invitrogen, Carlsbad, Calif., USA) for 18 hours at room temperature (FIG. 1).

The Gateway™ LR Clonase™ II Enzyme Mix LR contains the bacteriophage lambda recombination proteins Integrase (Int) and Excisionase (Xis), the E. coli-encoded protein Integration Host Factor (IHF) and reaction buffer. Gateway™ LR Clonase™ II Enzyme Mix catalyses the exchange of the DNA between the attL sites of the entry vector with the DNA between the attR sites in HSV1716GateRed DNA and was then destroyed by Proteinase K digestion.

The entire reaction mix was then added to 250 μl of serum free medium containing 10 μl lipofectamine 2000 and used to transfect 50% confluent BHK cells. After 4-6 hours the cells are DMSO-shocked and cultured at 37° C. for 48-72 hours. Cells were then harvested by scraping and, after 1 minute sonication in a sonicator bath, sequential 10-fold dilutions were plated out on Vero cells. After 72 hours, the plates were inspected by fluorescence microscopy and green plaques picked for further rounds of plaque purification.

Results

The site-specific recombination reaction was very efficient and at least 75% of viruses were gfp positive, meaning that only one further round of plaque picking is usually required for virus purification.

TABLE 1

Comparison of conversion efficiencies of HSV1716 from DSRed positive to GFP positive by site-specific and homologous recombination reactions.

| | pENTR1A-gfp | pRL1-del-PGK-gfp* | HSV1716GateRed DNA | % Red plaques | % green plaques |
|---|---|---|---|---|---|
| 1 | 8 μg | 0 | 0 | 0 | 0 |
| 2 | 0 | 0 | 5 μg** | 100 | 0 |
| 3 | 5 μg | 0 | 3 μg | 25 | 75 |
| 4 | 4 μg | 0 | 4 μg | 50 | 50 |
| 5 | 7 μg | 0 | 1 μg | 40 | 60 |
| 6 | 0 | 100 μg | 50 μg | 90 | 10 |

*Plasmid RL-1 del with PGK-gfp expression cassette inserted in MCS, used for homologous recombination, plasmid and viral DNA co-transfected into BHK cells.
**Viral DNA extracted from 4xT175 flasks 24 hours after infection with HSV1716gateRed virus, phenol/chloroform extracted and resuspended in 1 ml nuclease free water after isopropanol precipitation. Isolated DNA will not be exclusively viral but will include contaminating cellular DNA.

Notes on TABLE 1.
1. pENTR1A-gfp incubated overnight with LR Clonase ™ and transfected into BHK cells fails to produce any virus.
2. Viral DNA incubated overnight with LR Clonase ™ and transfected into BHK cells yields exclusively red plaques.
3-5. Co-incubation of pENTR1A-gfp and HSV1716gateRed with LR Clonase ™ followed by transfection into BHK cells yields both red and green plaques. Ratios vary with amounts of viral DNA/pENTR1A-gfp with optimum 75% green/25% red with 5 μg plasmid to 3 μg viral DNA.
6. Homologous recombination after co-transfection of RL1-del/PGK-gfp with HSV1716gateRed DNA results in low level of recombination (10%).

Purified gfp-positive virus was obtained from one round of plaque picking (which takes 1 week) following the site specific recombination reaction 4 in Table 1 compared with 5 rounds of plaque picking (=5 weeks) that were required to isolate a gfp-positive virus from the homologous recombination reaction.

12 different HSV1716 variants have been isolated following site specific recombination between the gene of interest in pENTR1A-gfp and HSV1716gateRed DNA and in each case, purified virus has been obtained after one round of plaque picking. This contrasts with at least 30 different HSV1716 variants generated by homologous recombination which have required a minimum of 5 but in some cases up to twelve rounds of plaque picking to isolate purified virus.

Discussion

The site specific recombination method described provides a simple, straightforward and convenient procedure for the generation of mutant HSV and avoids complex multi-step procedures. A single in vitro recombination reaction circumvents the need for in vivo recombination in bacteria or tissue culture cells.

Isolation of recombinant viruses is very rapid with stocks of the HSV mutant are usually produced within 3-4 weeks compared to between 3-6 months using RL1-del/homologous recombination.

Homologous recombination using RL1-del/PGK-gfp with HSV1716GateRed DNA resulted in 10-20% gfp-positive plaques compared to 75% gfp-positive plaques with pENTR1A-gfp site-specific recombination. Additionally, any contaminating non-recombinant viruses can be readily observed by fluorescence microscopy.

RL1-del is a large plasmid (circa. 8 Kbp) and cloning additional DNA into it is technically difficult. The entry vector pENTR1A-gfp is much smaller (circa. 4 Kbp) and cloning additional genes/DNA sequences into it is much easier.

The LR Clonase™ reaction uses very small amounts of viral DNA/entry plasmid. Typically, 3 μg of viral DNA and 5 μg entry vector is required for a site-specific recombination reaction compared to co-transfection of 50 μg viral DNA with 100 μg or 200 μg RL1-del for homologous recombination.

EXAMPLE 2

Method

The HSV1716GateRed variant with Gateway destination sites in the ICP34.5 deleted region was created as follows. The Gateway Vector Conversion system (Invitrogen Paisley, UK) provided DNA with attR site-specific recombination sequences for insertion into a vector of choice and was ligated into the EcoRV-digested and alkaline phosphatase treated plasmid sp73 (Promega) to create sp73gate. Once inserted in the plasmid, the DNA between the attR sites, encoding chloramphenicol resistance and the ccdB gene, was removed by Not1/BstXI digestion, the vector backbone was then blunt-ended with Klenow and alkaline phosphatase treated. The 1.3 kbp CMV-DSred expression cassette was excised from the plasmid pCMV-DsRed-Express (BD Biosciences, UK) by AflII/NsiI digestion, blunt ended by Klenow and ligated into the sp73gate backbone to create the plasmid sp73gatered. The attR sites and intervening CMV-DSred expression cassette was then excised from sp73gatered by BglII/XhoI digestion, blunt-ended with Klenow and ligated into the blunt-ended, alkaline phosphatase-treated BglII site in the plasmid RL1-del, used for the production of HSV1716 variants by homologous recombination. RL1-del (FIG. 2) is a cloning vector suitable for generating ICP34.5 null HSV-1 consisting of an HSV-1 DNA fragment containing the RL1 gene and its flanking sequences with the majority of the ICP34.5 open reading frame removed and replaced with a multi-cloning sequence (MCS). The transgene to be inserted into the RL1 loci is ligated into the MCS of RL1-del and homologous recombination with HSV-1 DNA, driven by the RL1 flanking sequences, results in concomitant deletion of the ICP34.5 gene and incorporation of the desired transgene. RL1-del contains the HSV-1 BamHI k DNA fragment (123459-129403) which includes the RL1 gene and its flanking sequences cloned into the BamHI site of plasmid pGem-3Zf (Promega). The 477 bp PflMI/BstEII fragment from the RL1 ORF (125292-125769) has been removed to inactivate the ICP34.5 gene and replaced with a MCS. The resultant plasmid, RL1-del/gatered was used to create HSV1716GateRed which contained the CMV-DSred expression cassette, flanked by attR destination sites in the RL1 loci by homologous recombination.

Approximately 50 μg of RL1-del/gatered were linearized by XmnI digestion and were cotransfected into BHK cells with HSV-1 17+DNA. RL1-del/gatered and viral DNA (c100 μg) were mixed with 20 μl lipofectamine 2000 (Invitrogen) in 250 μl DMEM/F12 (Invitrogen) serum-free medium and added to a 60 mm plate which contained 50% confluent BHK cells. After 4 hours of incubation at 37° C., the medium was removed and the cells shocked for exactly 4 minutes with 25% DMSO. After 3 washes with 5 ml culture medium the cells were returned to 37° C. with 5 ml GMEM supplemented with 10% newborn calf serum (both Invitrogen) and left for 72 hours. Cells were then scraped into the supernatant, sonicated in a sonicator bath for 2 minutes and stored at −70° C. until required. Serial dilutions were plated out on Vero cells in 60 mm plates, individual red fluorescent plaques were picked, added to 1 ml culture medium and sonicated in a sonicator bath for 2 minutes before serial dilutions were again plated out on Vero cells. Plaque purification was repeated 6 times before stocks of HSV1716GateRed were produced.

The pENTR1A was modified as follows. The DNA between the attL sites in pENTR1A was removed by EcoR1 digestion and the resulting vector backbone was blunt-ended and alkaline phosphatase treated. A green fluorescent protein expression cassette was inserted into the pENTR1A backbone by ligating it with the 1.3 kbp blunt-ended EcoRI/AflII fragment that contains the PGK promoter/gfp gene excised from the vector pSNRG (OligoEngine, Seattle, Wash., USA). Although EcoR1 digestion removed the ccdB gene from pENTR1A, a number of other restriction sites between the attL flanking sequences were retained for insertion of additional gene/DNA sequences of interest to be cloned into HSV1716 alongside the PGK-gfp expression cassette.

HSV1716GateRed DNA was obtained by phenol/chloroform extraction from 4×T175 flasks 24 hours after infection with the HSV1716GateRed virus and was resuspended in 1 ml nuclease free water. Approximately 1, 3 or 4 µg viral DNA were mixed with 7, 5 or 4 µg pENTR1Agfp and after overnight incubation with LR clonase the enzymes were inactivated by digestion with 1 µg Proteinase K for 10 minutes at 37° C. The entire reaction mix (11 µl) was added to 250 µl of serum free DMEM/F12 (Invitrogen) medium containing 10 µl lipofectamine 2000 and used to transfect 50% confluent BHK cells in a 60 mm dish. After 4-6 hours the cells were DMSO-shocked in 25% DMSO/PBS, washed and then cultured in 5 ml of GMEM at 37° C. for 48-72 hours. Control transfections comprising either 8 µg pENTR1Agfp or 5 µg HSV1716GateRed DNA incubated alone with the LR clonase mix were performed also and, for comparison with in vivo homologous recombination, 50 µg of the RL1-del shuttle vector with an inserted PGK-gfp expression cassette were cotransfected with 100 µg HSV1716GateRed DNA. Cells were then harvested by scraping into the medium and, after 1 minute sonication in a sonicator bath, 5 sequential 10-fold dilutions were plated out on Vero cells. After 72 hours, fluorescence microscopy was used to estimate the numbers of green and red plaques on each plate. For site specific recombination reactions using pENTR1A-gfp with additional DNA inserts, 5 µg plasmid were incubated with 3 µl HSV1716GateRed DNA.

Viral DNA was prepared using a Wizard SV genomic DNA kit from BHK cells 24 hours after infection with the relevant viruses at 5 pfu/cell and 20 µl extracted DNA was used as template for amplification by RL1 PCR. In addition to the viral DNA, the 50 µl PCR mix contained 24M primer R13, 14 µM primer F3, 1 mM Mg$^{2+}$, 200 µM each of dATP, dGTP, dCTP, dTTP, 200 µM deazaGTP and 1.25 U Platinum Pfx DNA polymerase (Invitrogen). The F3 primer sequence is CAGGCACGGCCCGATGACCGCCTC (SEQ ID No. 5) corresponding to bases 125172-125195 and complementary to bases 1176-1199 of the HSV strain 17+ sequence. Primer R13 sequence is GGCCAGACGCCGAAAACG (SEQ ID No. 6), complementary to bases 126035-126052 and corresponding to bases 319-336 of the HSV strain 17+ sequence. Primer F3 is positioned in the ICP34.5 coding region towards the 3'-end which is still present in HSV1716 and primer R13 lies outside the ICP34.5 ORF within the a sequence. The conditions for PCR were 94° C. for 2 minutes then 35 cycles of 94° C. for 15 seconds, 72° C. for 1 minute and 72° C. for 1 minute with a final extension of 72° C. for 2 minutes. Samples were then analysed on 1% agarose gels.

Results

We have described a highly efficient and extremely rapid site specific recombination method for the production of second generation variants of oncolytic HSV1716. Using an HSV1716 variant in which Gateway destination sequences were incorporated into the ICP34.5 deleted region we were able to derive recombinant viruses by simply incubating the viral DNA with the gene/DNA sequence of interest cloned into a Gateway entry plasmid and the relevant recombinase enzyme. As well as inserting the gene/DNA sequence of interest, site specific recombination also replaced a DsRed expression cassette with a green fluorescent protein expression cassette and, after the recombination reaction and transfection of the viral DNA into BHK cells, novel recombinant viruses were readily isolated by a single round of plaque purification.

We investigated the use of site-specific recombination in vitro for the production of HSV1716 variants and, most surprisingly, we were able to develop a rapid method which allowed exceedingly efficient production of second generation HSV1716 recombinants.

Figure 3:
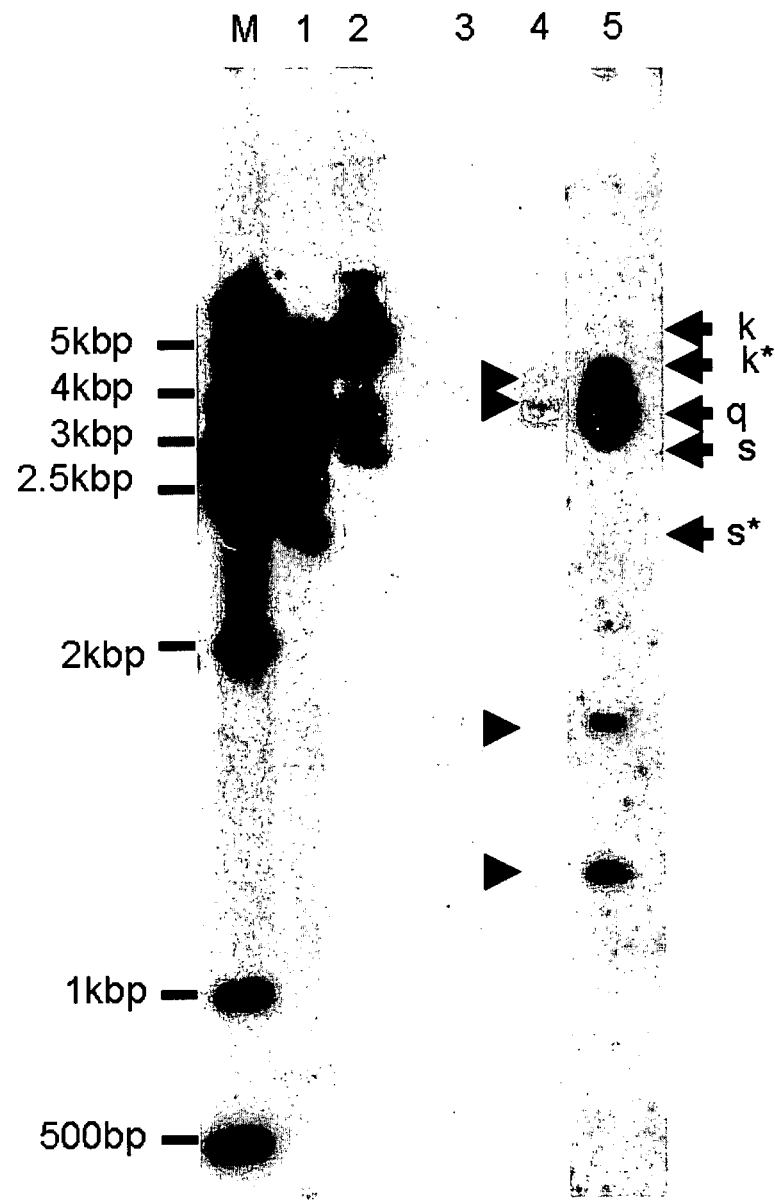

An HSV1716 variant, HSV1716GateRed, which contained a Gateway (Invitrogen, Paisley, UK) destination site located within the ICP34.5 deleted region was created using homologous recombination. The presence of the DsRed expression cassettes in both of the RL1 loci of HSV1716 was confirmed by Southern blotting (FIG. 3) using the ICP34.5-containing plasmid pGEM34.5 (McKie et al 1994). The ICP34.5 probe hybridizes with three main fragments in BamHI-digested HSV-1 17+DNA (FIG. 3, lane 2), termed k, q and s which have sizes of 5.9 kbp, 3.4 kbp and 2.9 kbp respectively. The ICP34.5 deletion in HSV1716 reduces the sizes of k and s to 5.2 kbp (k*) and 2.2 kbp (s*) respectively (FIG. 3, lane 1) with band q unaffected. Insertion of the DsRed expression cassette by homologous recombination with concomitant deletion of the ICP34.5 ORF introduced an additional BamHI site and, consistent with its incorporation into both RL1 loci, the k and s fragments are no longer detected and are replaced with novel bands of approximately 3.5 kbp, 3.0 kbp, 1.9 kbp and 1.5 kbp (FIG. 3, lanes 4 and 5). The latter two bands are only faintly visible in FIG. 3, lane 4 but are more clearly observed in the longer exposure shown in lane 5. Combined insertion of the 1.3 kbp DsRed expression cassette with the ICP34.5 deletion increases the sizes of k and s to 6.6 kbp and 3.6 kbp respectively in HSV1716GateRed but the additional BamHI site within the insert DNA results in cleavage to generate novel DNA fragments whose sizes are approximately equivalent to those shown in FIG. 3, lanes 4 and 5, with the 3.5 kbp/3.0 kbp and 1.9 kbp/1.5 kbp bands comprising the HSV1716GateRed k and s respectively.

The Gateway entry plasmid pENTR1A (Invitrogen) was modified to create a vector, pENTR1A-gfp, suitable for site specific recombination reactions with HSV1716GateRed.

Figure 4:
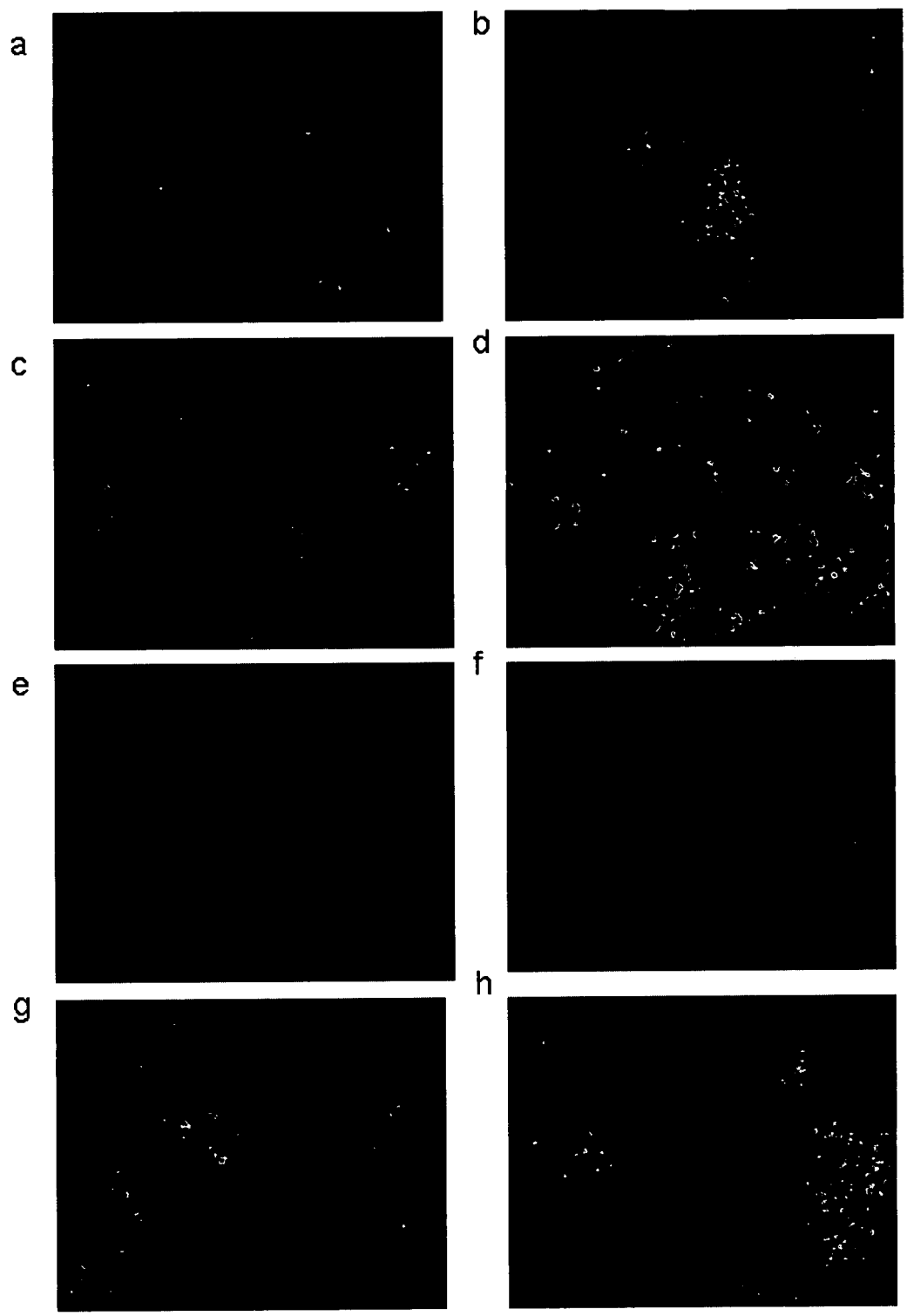

Initially, an HSV1716gfp recombinant was produced by incubating HSV1716GateRed DNA with the pENTR1A-gfp plasmid and the LR Clonase II enzyme mix (Invitrogen) for 18 hours at room temperature. In vitro site specific recombination between HSV1716GateRed DNA and pENTR1A-gfp is manifest by conversion of DsRed expressing viruses to viruses expressing gfp and this switch was readily monitored by fluorescent microscopy. Site-specific recombination between 1, 3 or 4 µg viral DNA and 7, 5 or 4 µg pENTR1A-gfp respectively resulted in approximately 50%, 80% or 70% conversion of DsRed to gfp expressing viruses respectively, as shown by the ratios of green to red plaques in FIG. 4, a-c. This compares very favourably with approximately 5% conversion using in vivo homologous recombination between HSV1716GateRed DNA and the RL1 shuttle plasmid with an inserted PGK-gfp expression cassette, only a single gfp-positive plaque is visible in FIG. 4f. Only DsRed expressing viruses were obtained after incubating 5 µg HSV1716GateRed DNA overnight with LR clonase (FIG. 4d) and no viruses were produced following overnight incubation of 8 µg pENTR1A-gfp with LR clonase (FIG. 4e). Therefore, the in vitro site-specific recombination reaction was very efficient and converted up to 80% of viral DNA from DsRed to gfp expression. Several gfp-positive plaques picked from the serially diluted plates were 100% pure as fluorescent microscopy of BHK cells infected with the plaque-picked viruses showed no contaminating DsRed expressing viruses (data not shown) and these were used for virus stock production. In contrast, isolation of a gfp-positive virus from the much less efficient homologous recombination required 6 consecutive rounds of plaque purification to remove all DsRed expressing viruses.

The plasmid pENTR1A-gfp has additional cloning sites both upstream and downstream of the PGK-gfp expression cassette and, following ligation of 250 bp, 500 bp, 1500 bp and 2000 bp DNA inserts into these sites, the efficiency of the site specific recombination reaction to generate HSV1716 recombinants with additional DNA inserts was investigated. Using 5 µg of plasmid with 3 µg HSV1716GateRed DNA, in vitro site specific recombination reactions resulted in 70-90% conversion of DsRed to gfp-expressing viruses as assessed by fluorescent microscopy (FIGS. 4g and h). Depending on the insert size, some variation in recombination efficiencies was observed with 250 bp (not shown) or 500 bp (FIG. 4g) inserts generating 80-90% HSV1716 recombinants whereas recombinations with 1500 bp (not shown) and 2000 bp (FIG. 4h) DNA inserts were slightly less efficient with approximately 70-80% conversion. The upstream or downstream location of the insert relative to the PGK-gfp expression cassette had no influence on recombination efficiencies (data not shown). Irrespective of the insert sizes, in most cases, a single plaque picked from the serially diluted plates was 100% pure with no DsRed virus contamination and was used for HSV1716 recombinant stock production. Occasionally, a low level (<1%) of DsRed-positive virus contamination was observed but this was easily removed by a further single round of plaque purification.

Figure 5:
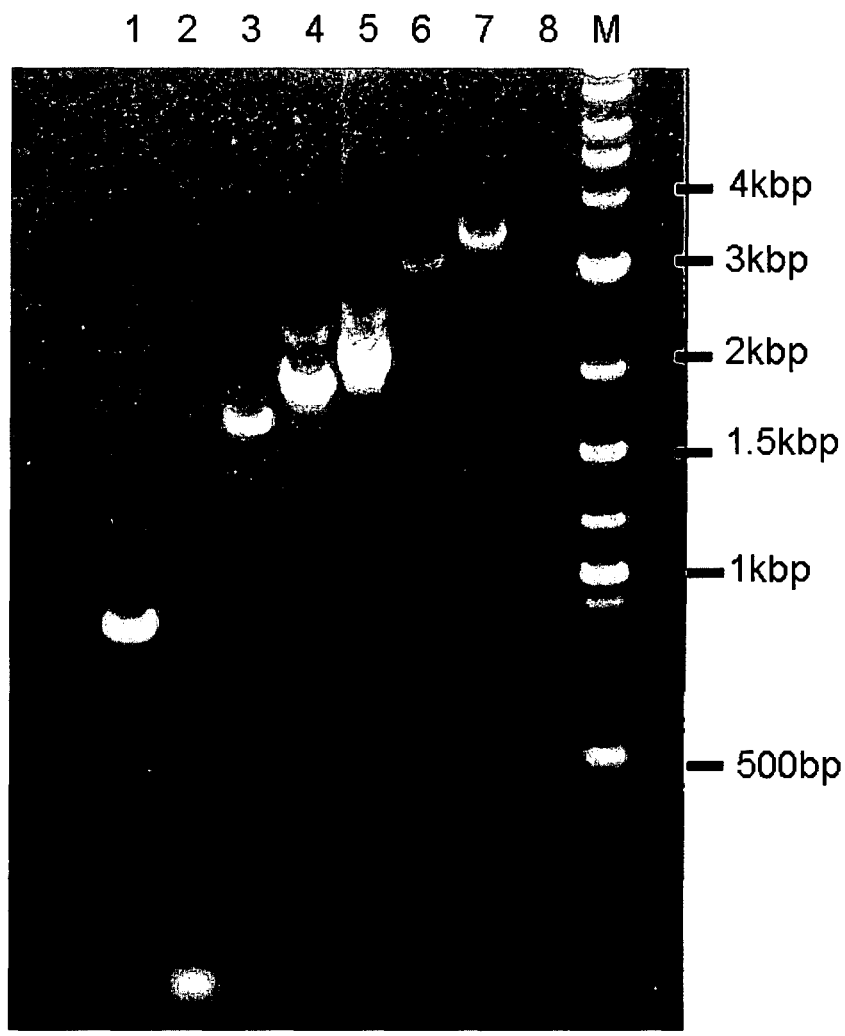

The genotype of the purified HSV1716 recombinants was confirmed using PCR with viral DNA as template and primers designed to amplify across the HSV1716 ICP34.5 deletion (FIG. 5). PCR with HSV-1 17+DNA as template generated an 850 bp band (lane 1) whereas amplification from HSV1716 DNA resulted in a 120 bp band (lane 2); these sizes are consistent with the wild type and deleted ICP34.5 gene. PCR amplification of viral DNA from HSV1716 recombinants generated using pENTR1A-gfp and pENTR1A-gfp with 250 bp, 500 bp, 1500 bp or 2000 bp inserts produced 1500 bp (lane 3), 1700 bp (lane 4), 2000 bp (lane 5), 3000 bp (lane 7) or 3500 bp (lane 8) bands respectively and again, these sizes correspond well with the additional insert plus the PGK-gfp expression cassette. Only a weak 1500 bp band was detected when the PCR was performed using HSV1716GateRed DNA as template (not shown), most likely because the attR sites immediately adjacent to the RL1 primer sites in HSV1716GateRed DNA have a detrimental effect on PCR which, as clearly shown in FIG. 5, is negated following the sequence changes resulting from recombination with the attL sites in pENTR1A-gfp.

Figure 6:
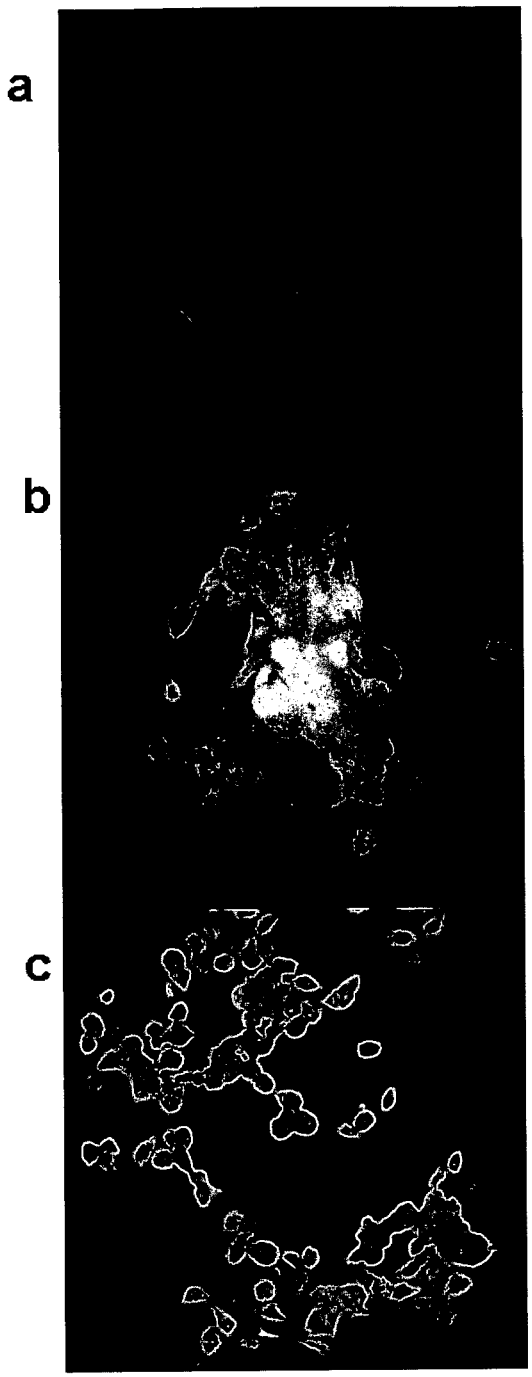
Figure 7:
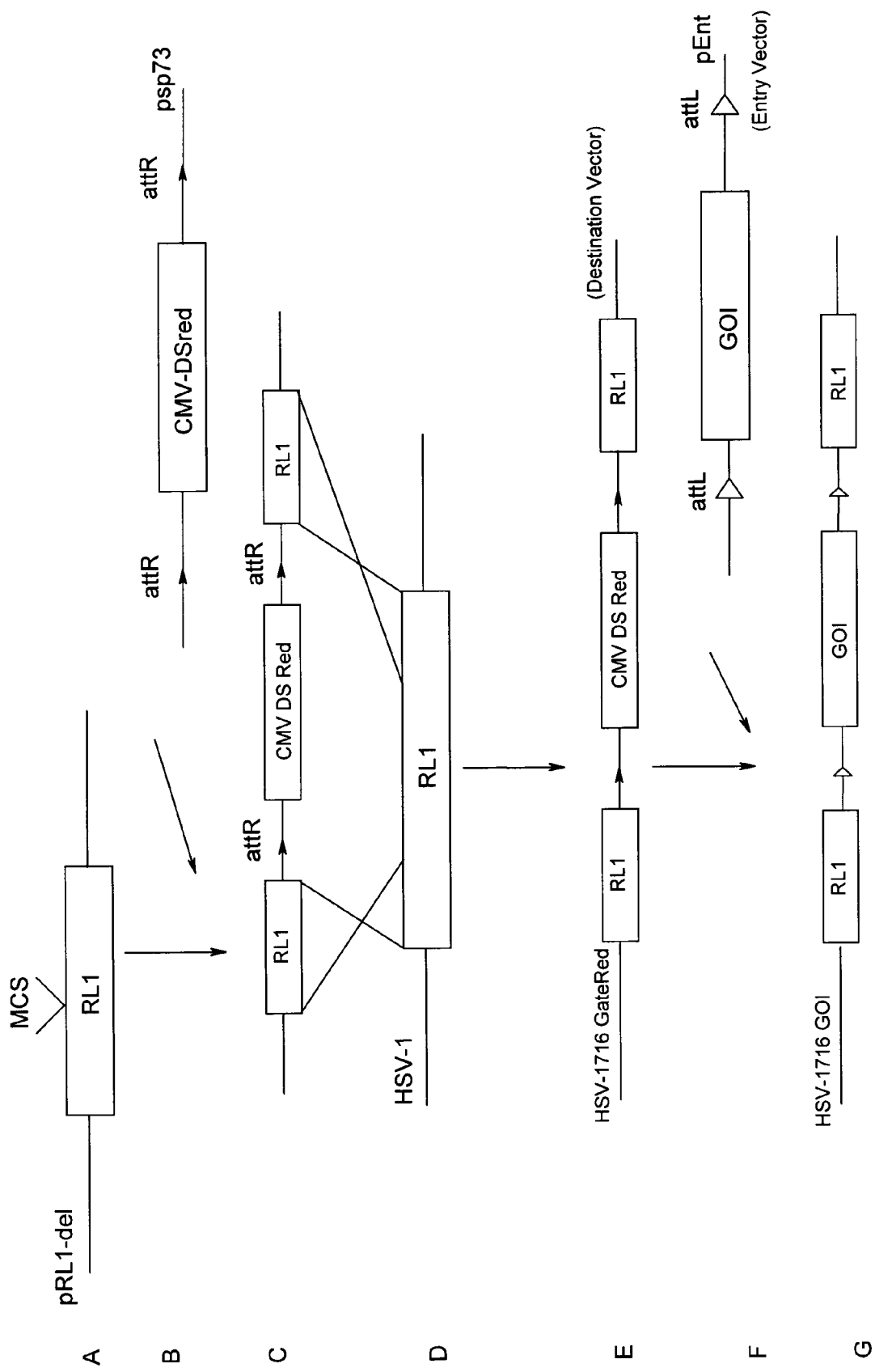

Oncolytic HSV1716 has immense therapeutic potential in the treatment of many forms of cancer and its potent ability to destroy tumour cells will be enhanced by variants that encode additional cytotoxic agents. Such agents include enzymes for the activation of prodrugs, transporters for the specific uptake of radiolabelled compounds, antisense/siRNAs directed against oncogenes and expression cassettes for tumour suppressor genes. Previously, to generate such variants, we have used RL1 shuttle vectors and homologous recombination which results in simultaneously ICP34.5 gene ablation and transgene incorporation. However there are a number of technical problems associated with this approach, principally that homologous recombination uses cotransfection of plasmid with large amounts of viral DNA and, since, at best, only 1 in 20 viruses produced are recombinants, purification from high levels of contaminating wild-type usually requires between 6 and 10 rounds of time-consuming plaque picking. Typically, after homologous recombination, isolation of the relevant HSV1716 variant for stock production usually requires 4-6 weeks. Our novel site specific recombination method provides a straightforward and convenient procedure, with a simple bench top incubation of viral and plasmid DNA with recombinase enzymes, for the generation of HSV1716 variants and avoids complex multi-step and technically demanding protocols. A single in vitro recombination reaction circumvents the need for any in vivo recombination in bacteria or tissue culture cells and variants are typically isolated in 5-7 days. Also the efficiency of the recombination reaction was not affected by a variety of differently sized DNA inserts, the largest of which, 2000 bp, consisted of the expression cassette for a 50 kDa protein which was readily detected by Western blotting of virally infected cell extracts (data not shown). Other advantages of the method include the use of very small amounts of viral DNA/entry plasmid such that the amount of HSV1716GateRed DNA isolated from 4×T175 flasks was sufficient for 350 recombination reactions, and easy detection of contaminating non-recombinant DsRed viruses by fluorescence microscopy. The advantages of fluorescent microscopy for visualisation of viral products from the site specific recombination reaction are clearly demonstrated in FIG. 6.

Recently, Terada et al (2006) described a rapid method to generate oncolytic HSV vectors, called HSV/Quik, which used two components consisting of the required HSV genome cloned in a BAC and a replication conditional shuttle plasmid which contained the DNA to be incorporated into the HSV variant. In their system, the HSV genome/BAC component comprised the ICP34.5 deletion mutant MGH1 DNA with two site specific recombination sequences, FRT and loxP, both in the UL39 gene, and transformation of bacteria with this BAC plus an appropriate shuttle plasmid resulted in FRT-mediated exchange of the relevant DNA sequence from the shuttle plasmid into the UL39 gene. After BAC isolation, residual prokaryotic sequences were removed by transfection of Vero cells with the BAC DNA plus a Cre recombinase expression plasmid. After several days in culture, recombinant viruses were produced. Although the whole procedure is rapid (7-10 days), the system is a multi-step procedure that requires two in vivo recombination reactions with associated transformation/transfection and an intervening plasmid isolation. Although our method also uses site specific recombination with HSV1716 variants generated in 5-7 days, a single step recombination in vitro dispenses with the need for in vivo bacterial and mammalian cell recombination reactions allowing our straightforward procedure to facilitate greatly the accelerated production of many 2$^{nd}$ generation HSV1716 variants to screen for improved tumour killing.

REFERENCES

1. B L Liu, M Robinson, Z-Q Han, R H Branston, C English, Preay, Y McGrath, S K Thomas, M Thornton, P Bullock, C A Love and R S Coffin; Gene Therapy (2003) 10, 292-303.
2. Terada, K., Wakimoto, H., Tyminski, E., Chiocca, E A and Saeki, Y. Development of a rapid method to generate multiple HSV vectors and their in vivo evaluation using syngeneic mouse tumor models. Gene Therapy 2006, 13: 705-714.
3. Maclean, A. R., Fareed, M U, Robertson, L., Harland, J. and Brown, S M (1991) Herpes simplex virus type 1 deletion variants 1714 and 1716 pinpoint neurovirulence related sequences in Glasgow strain 17+ between immediate early gene 1 and the "a" sequence. J. Gen Virol. 72, 631-639.
4. Brown, S M, Harland, J., Maclean, A R, Podlech, J. and Clements, J B. (1994) Cell type and cell state determine differentiated in vitro growth of non-neuroviulent ICP34.5-negative herpes simplex virus. J. Gen Virol. 75, 2367-2377.
5. Brown, S. M., MacLean, A. R., McKie, E. A. and Harland, J. (1997) The herpes simplex virus virulence factor ICP34.5 and the cellular protein MyD116 complex with proliferating cell nuclear antigen through the 63-amino acid domain conserved in ICP34.5, MyD116 and GADD34. J. Virol. 71, 9442-9449.
6. Harland, J., Dunn, P., Cameron, E., Conner, J. and Brown, S. M. (2003) The herpes simplex virus (HSV) protein ICP34.5 is a virion component that forms a DNA-binding complex with proliferating cell nuclear antigen and HSV replication proteins. J. Neurovirol. 9, 477-488.
7. Kesari, S., Randazzo, B P, Valyi-Nagy, T. (1995) A mutant herpes simplex virus replicates in brain tumours but not in neurons derived from a human embryonal carcinoma cell line. Lab Invest. 73, 636-648.
8. MacKie E A. et al. (1996) Selective in vitro killing of primary CNS tumours using herpes simplex virus type 1 (HSV-1) ICP34.5 null mutants—a potentially effective clinical therapy. Br J. Cancer 1996, 74, 745-752.
9. Randazzo, B P, Bhar, M G, Kesari, S., Fraser, N R, Brown, S M (1997) Treatment of experimental subcutaneous human melanoma with a replication restricted herpes simplex virus mutant J. Invest Dermatol. 108, 933-937.
10. Rampling, R, Cruikshank, G, Papanastassiou, V, Nicoll, J, Hadley, D, Brennan, D, Petty, R, MacLean, A, Harland, J, McKie, E, Mabbs, R and Brown, M (2000) Toxicity evaluation of replication-competent herpes simplex virus (ICP 34.5 null mutant 1716) in patients with recurrent malignant glioma. Gene Therapy 7 (10) 859-866.
11. Papanastassiou V, Rampling R, Fraser M, Petty R, Hadley D, Nicoll J, Harland J, Mabbs R, Brown M. (2002). The potential for efficacy of the modified (ICP 34.5(−)) herpes simplex virus HSV1716 following intratumoural injection into human malignant glioma: a proof of principle study. Gene Therapy: 9(6), 398-406.
12. Harrow, S., Papanastassiou, V., Harland, J., Mabbs, R., Petty, R., Fraser, M., Hadley, D., Patterson, J., Brown, S. M. and Rampling, R. (2004) Gene Therapy 11, 1648-1658.
13. MacKie, R M, Stewart, B and Brown, SM. (2001) Intralesional injection of herpes simplex virus 1716 in metastatic melanoma. The Lancet 357, 525-526.
14. Quigg, M., Mairs, R. J., Brown, S. M., Harland, J., Dunn, P., Rampling, R., Livingstone, A., Wilson, L. and Boyd, M. Assessment in vitro of a novel therapeutic strategy for glioma, combining herpes simplex virus HSV1716-mediated oncolysis with gene transfer and targeted radiation Med. Chem. (2005); 1: 423-429.
15. McKie, E. A., Hope, R. G., Brown, S. M. and MacLean, A. R. Characterization of the herpes simplex virus type 1 strain 17+ neurovirulence gene RL1 and its expression in a bacterial system. *J. Gen. Virol.* 1994; 75: 733-741.

---

The invention claimed is:

1. A method of generating mutant Herpes Simplex Viruses (HSV) comprising a nucleic acid sequence of interest (NOI), the method comprising the steps of:
   (i) providing a nucleic acid vector, wherein said vector comprises nucleic acid encoding the site specific att recombination sequences attL1 and attL2 and a NOI, wherein said NOI is between said site specific recombination sequences;
   (ii) providing a recombinant HSV, the genome of said recombinant HSV comprising the site specific att recombination sequences attR1 and attR2;
   (iii) contacting said nucleic acid vector of (i) with said recombinant HSV of (ii) together with one or more recombinase enzymes capable of catalyzing site specific recombination between the att site specific recombination sequences of said nucleic acid vector and said recombinant HSV, wherein attL1 and attR1 sites and attL2 and attR2 sites, respectively, are recombined, thereby generating mutant HSV;
   (iv) performing at least one round of plaque purification of the mutant HSV from step (iii) and identifying mutant HSV which comprise the NOI, wherein the recombination reaction of step (iii) results in at least 75% of the mutant HSV containing the NOI after one round of plaque purification, and wherein steps (i)-(iii) are conducted in a cell-free system.

2. The method of claim 1, wherein the recombinant HSV of (ii) is generated by a method comprising the steps of:
   a) providing a nucleic acid vector comprising nucleic acid encoding a nucleotide sequence having 70-100% sequence identity or complementarity with a selected region of an HSV genome;

b) inserting said attR1 and attR2 att recombination sequences in the nucleotide sequence of a) to generate a modified nucleic acid vector;
c) contacting said modified nucleic acid vector from b) with the HSV genome of step a) under conditions in which homologous recombination between said nucleic acid vector and said HSV genome may occur;
d) identifying recombinant HSV comprising said attR1 and attR2 att recombination sequences in the recombinant HSV genome.

3. The method of claim 1, wherein the nucleic acid vector of (i) and/or the recombinant HSV of (ii) further comprise a nucleotide sequence coding for a detectable marker, wherein said detectable marker is located between the site specific att recombination sequences of (i) and/or (ii).

4. The method of claim 1, wherein the recombinant HSV of (ii) is not part of an artificial chromosome.

5. The method of claim 2, wherein the nucleic acid vector of (b) comprises a nucleotide sequence coding for a detectable marker, which is located between the site specific att recombination sequences.

* * * * *

SEQUENCE LISTING

```
<160> NUMBER OF SEQ ID NOS: 6

<210> SEQ ID NO 1
<211> LENGTH: 125
<212> TYPE: DNA
<213> ORGANISM: Artificial sequence
<220> FEATURE:
<223> OTHER INFORMATION: Synthetic sequence: Site specific recombination
      sequence attR1

<400> SEQUENCE: 1
acaagtttgt acaaaaaagc tgaacgagaa acgtaaaatg atataaatat caatatatta      60
aattagattt tgcataaaaa acagactaca taatactgta aaacacaaca tatccagtca     120
tattg                                                                 125

<210> SEQ ID NO 2
<211> LENGTH: 125
<212> TYPE: DNA
<213> ORGANISM: Artificial sequence
<220> FEATURE:
<223> OTHER INFORMATION: Synthetic sequence: Site specific recombination
      sequence attR2

<400> SEQUENCE: 2
catagtgact ggatatgttg tgttttacag cattatgtag tctgtttttt atgcaaaatc      60
```

```
taatttaata tattgatatt tatatcattt tacgtttctc gttcagcttt cttgtacaaa      120
gtggt                                                                  125

<210> SEQ ID NO 3
<211> LENGTH: 100
<212> TYPE: DNA
<213> ORGANISM: Artificial sequence
<220> FEATURE:
<223> OTHER INFORMATION: Synthetic sequence: Site specific recombination
      sequence attL1

<400> SEQUENCE: 3
caaataatga ttttattttg actgatagtg acctgttcgt tgcaacaaat tgataagcaa       60 tgcttttta taatgccaac tttgtacaaa aaagcaggct                             100

<210> SEQ ID NO 4
<211> LENGTH: 100
<212> TYPE: DNA
<213> ORGANISM: Artificial sequence
<220> FEATURE:
<223> OTHER INFORMATION: Synthetic sequence: Site specific recombination
      sequence attL2

<400> SEQUENCE: 4
acccagcttt cttgtacaaa gttggcatta taagaaagca ttgcttatca atttgttgca       60
acgaacaggt cactatcagt caaaataaaa tcattatttg                            100

<210> SEQ ID NO 5
<211> LENGTH: 24
<212> TYPE: DNA
<213> ORGANISM: Artificial sequence
<220> FEATURE:
<223> OTHER INFORMATION: Synthetic sequence: Primer F3

<400> SEQUENCE: 5
caggcacggc ccgatgaccg cctc                                              24

<210> SEQ ID NO 6
<211> LENGTH: 18
<212> TYPE: DNA
<213> ORGANISM: Artificial sequence
<220> FEATURE:
<223> OTHER INFORMATION: Synthetic sequence: Primer R13

<400> SEQUENCE: 6
ggccagacgc cgaaaacg                                                     18
```